US009352005B2

(12) United States Patent
Kim et al.

(10) Patent No.: US 9,352,005 B2
(45) Date of Patent: May 31, 2016

(54) **ISOLATED-PROBIOTICS PREPARATION CONTAINING *BACILLUS* SP. STRAIN**

(75) Inventors: Young Ok Kim, Busan (KR); Kyung Kil Kim, Busan (KR); Bo Hye Nam, Busan (KR); Sang Jun Lee, Busan (KR); Dong Gyun Kim, Busan (KR); Hyon Sob Han, Seoul (KR); Si Yong Yang, Incheon (KR); Hee Jeong Kong, Busan (KR); Woo Jin Kim, Busan (KR); Bong Seok Kim, Busan (KR)

(73) Assignee: REPUBLIC OF KOREA (REPUBLIC OF NATIONAL FISHERIES RESEARCH AND DEVELOPMENT INSTITUTE), Busan (KR)

( * ) Notice: Subject to any disclaimer, the term of this patent is extended or adjusted under 35 U.S.C. 154(b) by 0 days.

(21) Appl. No.: 13/885,832

(22) PCT Filed: Sep. 8, 2011

(86) PCT No.: PCT/KR2011/006655
§ 371 (c)(1),
(2), (4) Date: Jul. 30, 2013

(87) PCT Pub. No.: WO2012/067341
PCT Pub. Date: May 24, 2012

(65) Prior Publication Data
US 2013/0302299 A1 Nov. 14, 2013

(30) Foreign Application Priority Data

Nov. 16, 2010 (KR) ........................ 10-2010-0113932

(51) Int. Cl.
*A23K 1/00* (2006.01)
*A23K 1/18* (2006.01)
*C12R 1/07* (2006.01)
*A61K 35/742* (2015.01)

(52) U.S. Cl.
CPC ............... *A61K 35/742* (2013.01); *A23K 1/009* (2013.01); *A23K 1/188* (2013.01); *C12R 1/07* (2013.01)

(58) Field of Classification Search
CPC ......... A23L 1/00; A23L 1/3014; A23L 1/325; A23L 1/3252; A23L 1/326; A23K 1/00; A23K 1/006; A23K 1/008; A23K 1/009; C12N 1/00; C12N 1/20
See application file for complete search history.

(56) References Cited

U.S. PATENT DOCUMENTS

2004/0009160 A1* 1/2004 Villamar et al. ........... 424/93.46

FOREIGN PATENT DOCUMENTS

| JP | 63-209580 | 8/1988 |
| JP | 64-086842 | 3/1989 |

OTHER PUBLICATIONS

Kesarcodi-Watson, A. et al. 2008. Probiotics in aquaculture: The need, principles and mechanisms of action and screening processes. Aquaculture 274:1-14. specif. pp. 1, 3-4, 6-8.*
Balcazar, J.L. et al. Inhibitory activity of probiotic Bacillus subtilis UTM 126 against *Vibrio* species confers protection against vibnosis in juvenile shrimp (*Litopenaeus vannamei*) Current Microbiology 55: 409-412. specif. pp. 409-411.*
Robichon, D. et al. 1999. Atomic force microscopy imaging of dried or living bacteria.C.R. Academy of Sciences, Paris/Life Sciences 322:687-693. specif. p. 687.*

* cited by examiner

*Primary Examiner* — Renee Claytor
*Assistant Examiner* — Sharon M Papciak
(74) *Attorney, Agent, or Firm* — Stuart H. Mayer; Mayer & Williams PC

(57) ABSTRACT

The present invention relates to an isolated *Bacillus* sp. strain having probiotic activity. More particularly, the present invention relates to an isolated *Bacillus* sp. 2-4 (KCCM11107P) strain having probiotic activity. Since the strain of the present invention functions as probiotics by having an antibacterial activity against various fish pathogenic bacteria, as well as secreting helpful enzymes such as protease, amylase, cellulose, and lipase to help the digestion and absorption of the feed, the strain of the present invention can be helpfully used as a feed additive for fish and crustaceans.

1 Claim, 5 Drawing Sheets

```
AGAGTTTGATCCTGGCTCAGGACGAACGCTGGCGGCGTGCCTAATACATGCAAGTCGAGCGGAC
AGATGGGAGCTTGCTCCCTGATGTTAGCGGCGGACGGGTGAGTAACACGTGGGTAACCTGCCTG
TAAGACTGGGATAACTCCGGGAAACCGGGGCTAATACCGGATGGTTGTTTGAACCGCATGGTTC
AGACATAAAAGGTGGCTTCGGCTACCACTTACAGATGGACCCGCGGCGCATTAGCTAGTTGGTG
AGGTAACGGCTCACCAAGGCGACGATGCGTAGCCGACCTGAGAGGGTGATCGGCCACACTGGGA
CTGAGACACGGCCCAGACTCCTACGGGAGGCAGCAGTAGGGAATCTTCCGCAATGGACGAAAGT
CTGACGGAGCAACGCCGCGTGAGTGATGAAGGTTTTCGGATCGTAAAGCTCTGTTGTTAGGGAA
GAACAAGTGCCGTTCAAATAGGGCGGCACCTTGACGGTACCTAACCAGAAAGCCACGGCTAACT
ACGTGCCAGCAGCCGCGGTAATACGTAGGTGGCAAGCGTTGTCCGGAATTATTGGGCGTAAAGG
GCTCGCAGGCGGTTTCTTAAGTCTGATGTGAAAGCCCCCGGCTCAACCGGGGAGGGTCATTGGA
AACTGGGAACTTGAGTGCAGAAGAGGAGAGTGGAATTCCACGTGTAGCGGTGAAATGCGTAGA
GATGTGGAGGAACACCAGTGGCGAAGGCGACTCTCTGGTCTGTAACTGACGCTGAGGAGCGAAA
GCGTGGGGAGCGAACAGGATTAGATACCCTGGTAGTCCACGCCGTAAACGATGAGTGCTAAGTG
TTAGGGGGTTTCCGCCCCTTAGTGCTGCAGCTAACGCATTAAGCACTCCGCCTGGGGAGTACGG
TCGCAAGACTGAAACTCAAAGGAATTGACGGGGGCCCGCACAAGCGGTGGAGCATGTGGTTTAA
TTCGAAGCAACGCGAAGAACCTTACCAGGTCTTGACATCCTCTGACAATCCTAGAGATAGGACG
TCCCCTTCGGGGGCAGAGTGACAGGTGGTGCATGGTTGTCGTCAGCTCGTGTCGTGAGATGTTG
GGTTAAGTCCCGCAACGAGCGCAACCCTTGATCTTAGTTGCCAGCATTCAGTTGGGCACTCTAA
GGTGACTGCCGGTGACAAACCGGAGGAAGGTGGGGATGACGTCAAATCATCATGCCCCTTATGA
CCTGGGCTACACACGTGCTACAATGGACAGAACAAAGGGTAGCGAAACCGCGAGGTTAAGCCAA
TCCCACAAATCTGTTCTCAGTTCGGATCGCAGTCTGCAACTCGACTGCGTGAAGCTGGAATCGC
TAGTAATCGCGGATCAGCATGCCGCGGTGAATACGTTCCCGGGCCTTGTACACACCGCCCGTCA
CACCACGAGAGTTTGTAACACCCGAAGTCGGTGAGGTAACCTTTTAGGAGCCAGCCGCCGAAGG
TGGGACAGATGATTGGGGTGAAGTCGTAACAAGGTAACCGT
```

Fig 2

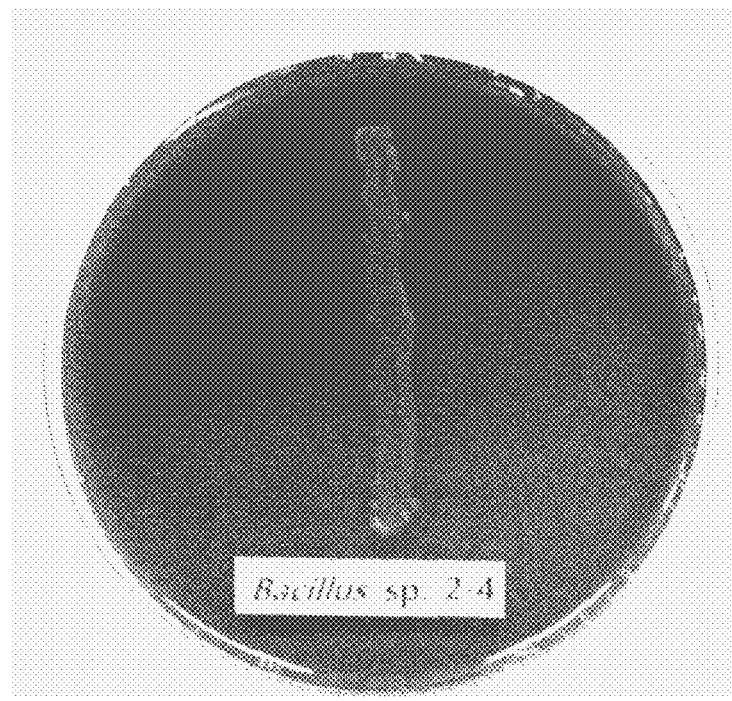

Fig 3

Skim milk :Protease   Tricaprylin :Lipase   Water-soluble starch :Amylase   CMC :CMCase

ISOLATED-PROBIOTICS PREPARATION CONTAINING *BACILLUS* SP. STRAIN

CROSS-REFERENCE TO RELATED APPLICATION

This application claims priority to Korean Patent Application No. 2010-0113932 filed on Nov. 11, 2010 and all the benefits accruing therefrom under 35 U.S.C. §119, the contents of which are incorporated by reference in their entirety.

BACKGROUND

The present invention relates to an isolated probiotics preparation containing *Bacillus* sp. strain and a use thereof.

Currently, aquaculture is done by mass rearing and high density breeding. Since farm-raised fish is exposed to a lot of stresses and pathogenic bacteria, various antibiotic products are administered in combination with feed, thus inducing the prevention of diseases and the improvement of the growth rate. However, the use of antibiotics in animals and fish for the prevention of diseases is recently restricted for the protection of environment, and also the legal restriction for the use of antibiotics is partially enforced. Thus, an attempt to use naturally derived probiotics instead of antibiotics is appeared, and practically, it has been reported that the effect was remarkable when *Lactobacillus* was administrated to animals and fish as probiotics (Simirnov, V. V. et al., *Microbiol. Z.* 55(4): 92, 1993).

Probiotics, live bacterial preparations, prevent the settlement of harmful bacteria since the live bacteria, which are administrated to the human and animal, are concentrated and settled down on the wall of the digestive tract in intestine. Also, probiotics play a role in preventing the growth of harmful bacteria by lowering the pH inside the intestine through production of lactic acids. Furthermore, the administrated live bacterial preparation produces bacteriocin or peroxides to suppress the proliferation of pathogens, and promotes the activity of intestinal villi which serves to absorb nutrients. In addition, the live bacterial preparation produces a substance which is helpful for the absorption and utilization of nutrients, improves feed conversion ratio, and produces a substance which neutralizes a toxin caused by the pathogens. The live bacterial preparation is mostly used to suppress the reduction of helpful bacteria in the digestive tract of animals or fish caused by stress, and prevents the settlement of pathogens by adhering to a wall of bacteria-free digestive tract before the pathogens adhere to the wall, after oral administration of antibiotic products.

However, since *Lactobacillus* has certain specificity with an enterocyte of an animal subjected to be used, due to its species-specificity, effects of preventing and treating diseases can be achieved only if *Lactobacillus* should not be excreted with feces as it proliferates but adsorbed in the intestine (Conway, P. L. et al., *J. Dairy Sci.,* 70:1, 1987). Nevertheless, most *Lactobacillus* sp, which are currently used as probiotics, are easily separated in the intestine of human and land animals, and are applied, as probiotics, to fish living and growing in the sea and fresh water as well, the human and land animals.

Moreover, the development of live bacterial preparations for livestock has been substantially studied in worldwide, and thereby a large number of products have been commercialized. However, live bacterial preparations for fish are few, and therefore, most recently used probiotics products exclusively used for fish in South Korea are strains imported from foreign countries, which are not adapted well to the domestic growth environment of fish. Also, since an origin of a microorganism used as probiotics for a marine fish is not a strain isolated from fish, but a strain isolated mostly from mammals, the probiotics are co-used for mammals, thus raising doubts about the effect when being applied to fish. In addition, the colony forming unit is low owing to the lack of stability caused by the time lag between import and domestic distribution because raw materials are imported. This is considered a significant problem.

Looking into related arts with regard to probiotics for fish in South Korea, Korean Patent Registration No. 206454 discloses a *Lactobacillus* sp. DS-12 strain isolated from an intestine of fish and probiotics using same, and Korean Patent Application Publication No. 2008-0104846 discloses a *Lactobacillus pentosus* PL-11 strain derived from *Anguilla japonica*, and probiotics for only *Anguilla japonica* using the same. However, the former does not have an antibacterial activity against the *Streptococcus* sp., which is causative bacteria of streptococcosis in *Paralichthys olivaceus* and *Seriola quinqueradiata*; and the later exhibits an antibacterial activity only in the case where a culture supernatant is treated with high concentration and also has a drawback of low availability in that it is used only for *Anguilla japonica*.

Thus, the specialized live bacterial preparations for fish, which overcome the problems above, is urgently needed domestically and globally.

SUMMARY

The present invention provides an isolated bacterial strain which can be used as a live bacterial preparation for fish and crustaceans.

The present invention also provides a probiotic preparation including the isolated bacterial strain.

The present invention also provides a feed additive including the isolated bacterial strain for fish and crustaceans.

The present invention also provides a feed including the isolated bacterial strain for aquaculture of fish and crustaceans.

The present invention also provides a method for preventing the farm-raised fish and/or crustaceans from massive death caused by a pathogen, using the feed.

TECHNICAL SOLUTION

In accordance with an example, the present invention provides an isolated *Bacillus* sp. 2-4 strain (KCCM11107P).

In accordance with an example, the present invention provides a probiotic preparation including the isolated strain.

In accordance with an example, the present invention provides a feed additive including the isolated strain for aquaculture of fish and/or crustaceans.

In accordance with an example, the present invention provides a feed including the feed additive for aquaculture of fish and/or crustaceans.

ADVANTAGEOUS EFFECTS

In accordance with an example, the present invention provides a method for preventing farm-raised fish and/or crustaceans from massive death caused by pathogens, the method including feeding farm-raised fish and/or crustaceans with the feed.

BRIEF DESCRIPTION OF THE DRAWINGS

Exemplary embodiments can be understood in more detail from the following description taken in conjunction with the accompanying drawings, in which:

FIG. 2 illustrates base sequence of 16S rDNA of the *Bacillus* sp. 2-4 strain of the present invention;

FIG. 3 is a photograph showing a hemolytic property of the *Bacillus* sp. 2-4 strain of the present invention;

DETAILED DESCRIPTION OF EMBODIMENTS

The present inventors provide an isolated *Bacillus* sp. 2-4 strain which can be used as probiotics.

The isolated *Bacillus* sp. 2-4 strain of the present invention is isolated from intestines of farm-raised shrimps. Particularly, the inventors selected 400 morphologically different strains using BHI and MRS agar medium in the intestine and pancreas obtained from an internal shrimp aquaculture farm. Then, the inventors selected a strain which had a remarkable antibacterial activity through antibacterial activity screening, and sequenced a base sequence of 16S rDNA of the strain (SEQ ID NO: 1). As a result, the inventors confirmed that the strain is an isolated strain which belongs to *Bacillus* sp. (see FIGS. 1 and 2).

The cell growth and antibacterial activity of the isolated *Bacillus* sp. 2-4 strain tend to be gradually lowered as a culturing time passed at the temperature of 30° C. (see FIG. 3); and the isolated *Bacillus* sp. 2-4 strain exhibits a strong antibacterial activity against *Edwardisella tarda*, *Streptococcus iniae* and *Vibrio anguillarum* which are typical fish pathogens, but exhibits a weak antibacterial activity against *Vibrio harveyi* and *Streptococcus parauberis* (see FIG. 4).

Figure 5:
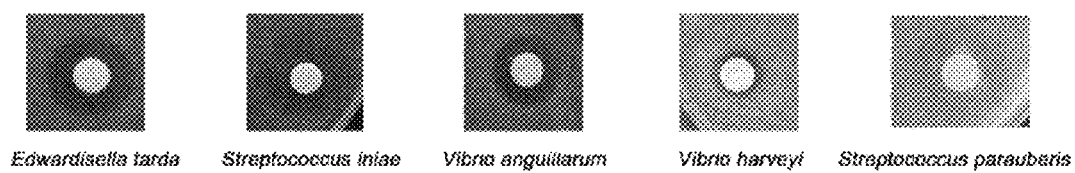
FIG. 5 is a photograph showing an antibacterial activity of the *Bacillus* sp. 2-4 strain of the present invention against fish pathogenic bacteria.

In addition, since the isolated *Bacillus* sp. 2-4 strain of the present invention secretes helpful enzymes such as protease, amylase, lipase, and CMCase, it is considered to be very appropriate for a feed additive (see FIG. 5).

To be used as the feed additive, a specific strain itself should not be pathogenic and should not influence the hatch of fish and the growth of rotifer and artemia which are used as feeds for fish and crustaceans. The isolated *Bacillus* sp. 2-4 strain of the present invention does not influence the hatch of *Paralichythys olivaceus* at all, and also does not have any influence on the vitality of rotifer and artemia (see Table 1 to 3).

Further, the isolated *Bacillus* sp. 2-4 strain of the present invention exhibits a remarkable probiotics effect in vivo. Particularly, the inventors of the present invention infect *Paralichythys olivaceus* with *E. tarda* of *Paralichythys olivaceus* by intraperitoneal injection, then feed *Paralichythys olivaceus* with feeds mixed with the isolated *Bacillus* sp. 2-4 strain, and thereafter investigate the number of dead individuals by comparing with the control group which is not feed with the *Bacillus* sp. 2-4 strain. Resultantly, it is confirmed that the number of dead individuals is significantly lower than that of the control group (see FIGS. 6 to 7).

Thus, it is considered that the isolated *Bacillus* sp. 2-4 strain of the present invention may be helpfully used as probiotics for aquaculture of fish and crustaceans. Therefore, the present invention provides a probiotic preparation including the *Bacillus* sp. 2-4 strain as an active ingredient. The probiotic preparation of the present invention may include, in addition to the above-described active ingredient, well-known carriers or additives which are pharmaceutically or cytologically acceptable or acceptable for feed.

Also, the present invention provides a feed additive including the *Bacillus* sp. 2-4 strain as an active ingredient. The feed additive of the present invention may include, in addition to the above-described active ingredient, additives such as well-known carriers or stabilizers which are pharmaceutically or sitologically acceptable or acceptable for feed. Also, if necessary, various nutrients (for instance, vitamins, amino acids, and a mineral), an antioxidant, an antibiotic, an antibacterial, and other additives may be added to the feed additive of the present invention. Also, the feed additive may be prepared in a suitable form such as powder, granular, pellet, and suspension. In the case of supplying the feed additive of the present invention, the feed additive can be supplied alone or supplied in combination with feed for fish or crustaceans.

Examples of fish, which is a subject of the present invention, may preferably include a marine fish such as sea bream, *Paralichythys olivaceus*, *Sebastes schelegeli*, *Pagrus major*, *Miichthys miiuy*, *Mugil cephalus*, and *Epinephelus septemfasciatus*, and land-based fish such as *Anguilla japonica*, *Plecoglossus altivelis*, *Oncorhynchus masou*, *Onchorhynchus mykiss*, and *Siniperca scherzeri*; and more preferably include *Paralichythys olivaceus*, *Sebastes schelegeli*, and *Pagrus major*, but not specifically limited thereto. Examples of crustaceans may preferably include shrimps such as *Litopenaeus vannamei*, *Marsupenaeus japonicus*, *Penaeus monodon*, *Penaeus chinensis*, *Penaeus morguiensi*, and brachyura such as *Eriocheir sinensis*, and *Portunus trituberculatus*; and more preferably include *Litopenaeus vannamei*; and most preferably include *Penaeus vannanei*, but not limited thereto.

Also, the present invention provides a feed including the *Bacillus* sp. 2-4 strain for aquaculture of fish and/or crustaceans. The *Bacillus* sp. 2-4 strain of the present invention, which is a gram positive bacterium having a sporulation capacity, is preferably formulated in a spore form, but not limited thereto. The feed of the present invention is not particularly limited, but any feed such as powder feed, solid feed, moist pellet feed, dry pellet feed, extruder pellet (EP) feed, and raw feed is available.

The present invention also provide a method for preventing farm-raised fish and/or crustacean from massive death caused by a pathogen, the method including feeding farm-raised fish and/or crustaceans with the feed.

In this case, the feed is preferably supplied with the same amount and at the same feeding interval as those of conventional feed. The pathogen is preferably *Edwardisella tarda*, *Streptococcus iniae*, *Vibrio* anguillarum, *Vibrio harveyi* or *Streptococcus parauberis*, and more preferably *Edwardisella tarda*, *Streptococcus iniae* or *Vibrio anguillarum*, but not limited thereto.

Hereinafter, the present invention will be described through specific examples. The examples are herein provided for describing the present invention, but the scope of the present invention is not limited to the examples below.

EXAMPLE 1

Isolation and Identification of Strain

Figure 1:
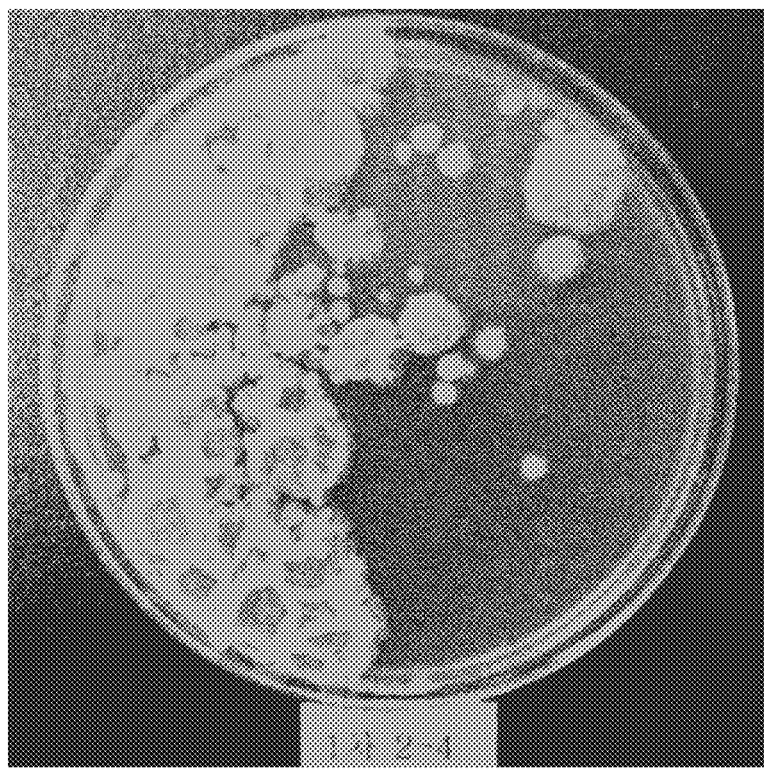
FIG. 1 is a photograph showing a cultured form of a *Bacillus* sp. 2-4 strain of the present invention in an agar medium.

To discover a noble strain which can be used as probiotics, the present inventors separated intestine and pancreas of shrimps obtained from the internal shrimp aquaculture farm, and then selected a strain having an outstanding antibacterial activity therefrom. Particularly, 400 strains, which were morphologically different, were primarily selected by spreading homogenates of intestine and pancreas of shrimps on the brain heart infusion (BHI) and de man, orgosa and sharpe (MRS) agar plate, and then culturing at 30° C. Subsequently, the strains were cultured in HBI and MRS media for 48 hours, and then the cultured supernatant was concentrated 5-fold. To measure the antibacterial activity, *Vibrio harveyi* was spread on BHI agar plate and 50 µl of concentrated culture supernatant was dispensed on a 0.8 cm paper-disk, and then the strains having the antibacterial activity were secondarily selected by forming an inhibitory zone. Among those strains, a strain having excellent antibacterial activity was finally selected (FIG. 1). This strain was a gram positive *Bacillus*, and the glucose fermentation pattern was analyzed with an API 50 CHB system (Korean Culture Center of Microorganism (KCCM)) for analyzing biochemical properties (Table 1). In addition, for molecular biological analysis, the base sequence of 16S rDNA was analyzed, and the result proved that the strain was a gram positive *Bacillus* which has 99% or more homology with the base sequence of 16S rDNA of *Bacillus subtilis* X-10 strain (FIG. 2). Based on these results, the isolated strain was designated as a *Bacillus* sp. 2-4 strain, and given with an accession number, KCCM11107P, by depositing the strain to the Korean Culture Center of Microorganisms with an address of 361-221, Yurim B/D Hongje-1-dong, Seodaemun-gu, SEOUL 120-091 Republic of Korea on Oct. 6, 2010. The deposited material has been accepted for deposit under the Budapest Treaty on the International Recognition of the Deposit of Microorganisms for the purpose of Patent Procedure and that all restriction on the availability to the public of the material so deposited will be irrevocably removed upon the granting of a patent.

TABLE 1

Glucose fermentation pattern analysis of *Bacillus* sp. 2-4 strain

| control | − | Esculine | + |
|---|---|---|---|
| Glycerol | + | Salicine | + |
| Erythritol | − | Cellobiose | + |
| D-Arabinose | − | Maltose | + |
| L-Arabinose | + | Lactose | + |
| Ribose | + | Melibiose | |
| D-Xylose | + | Saccharose | + |
| L-Xylose | − | Trehalose | |
| Adonitol | − | Inuline | |
| β-Methyl-xyloside | − | Melezitose | |
| Galactose | − | D-Raffinose | + |
| D-Glucose | + | Amidon | |
| D-Fructose | + | Glycogene | + |
| D-Mannose | + | Xylitol | |
| L-Sorbose | | βGentiobiose | |
| Rhamnose | | D-Turanose | |
| Dulcitol | | D-Lyxose | |
| Inositol | + | D-Tagatose | |
| Mannitol | + | D-Fucose | |
| Sorbitol | + | L-Fucose | |
| α-Methyl-Dmannoside | | D-Arabitol | |
| α-Methyl-glucoside | + | L-Arabitol | |
| N-Acetyl glucosamine | | Gluconate | |
| Amygdaline | + | 2 ceto-gluconate | |
| Arbutine | + | 5 ceto-gluconate | − |

+: positive,
−: negative

EXAMPLE 2

Analysis of Hemolytic Property

β-hemolysis is an action which hemolyzes red blood cells by hydrolyzing phospholipids supplied from red blood cells by producing phospholipids enzyme in harmful bacteria. To investigate the hemolytic property of *Bacillus* sp. 2-4 strain of the present invention, TSA (Difco, USA), which contained 5% of sheep blood (KisanBiotech, Korea), was produced. The *Bacillus* sp. 2-4 strain was streaked on the produced blood agar medium, and then cultured at 37° C. for 24 hours. The result demonstrated that the *Bacillus* sp. 2-4 strain did not exhibit the hemolytic property as shown in FIG. 3, and thus considered a nonpathogenic and stable strain.

EXAMPLE 3

Antibacterial Activity Analysis

The present inventors analyzed the antibacterial activity of the *Bacillus* sp. 2-4 strain through various methods.

Figure 4:
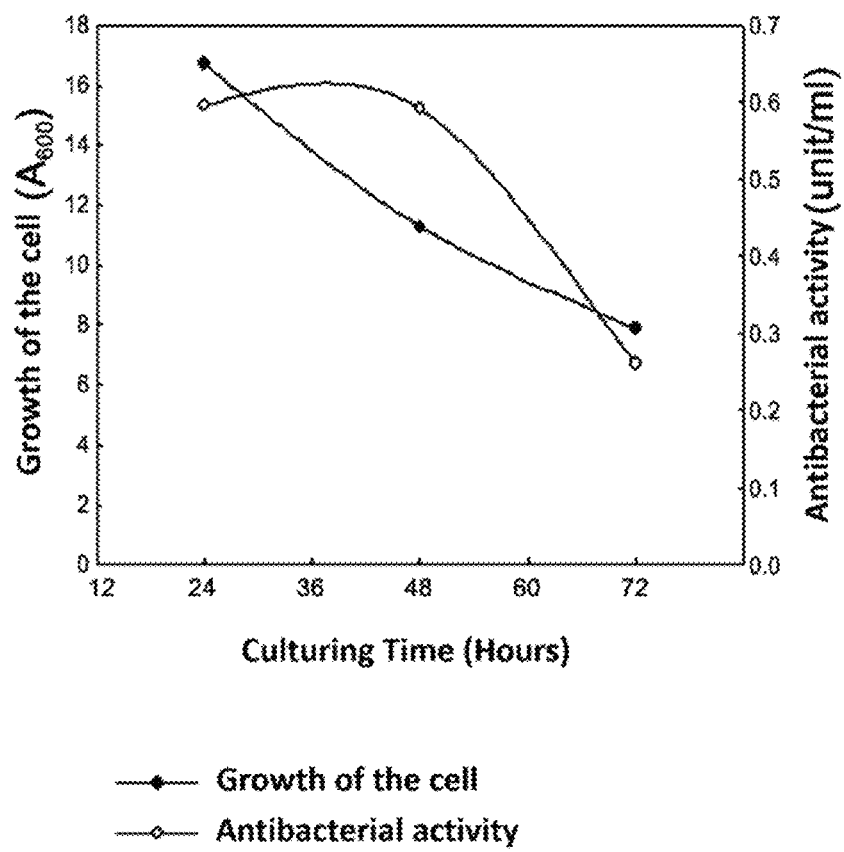
FIG. 4 is a graph illustrating a cell growth and an antibacterial activity versus the time for culture of the *Bacillus* sp. 2-4 strain of the present invention.

First of all, the antibacterial activity versus a culturing time was investigated while culturing the *Bacillus* sp. 2-4 strain of the present invention after re-inoculating 1% of the *Bacillus* sp. 2-4 strain in a BHI medium at 30° C. (FIG. 4). The antibacterial activity was quantitatively measured in a manner such that absorbances of the culture medium of a control group and an experimental group were measured every time point and a value lowered than the absorbance at 600 nm by 0.01 was calculated as 1 unit. Herein, only *V. harveyi* was cultured in the control group, whereas the strain of the present invention was co-cultured with *V. harveyi*. As a result, the strong antibacterial activity was achieved until 48 hours, but the antibacterial activity was decreased as the culturing time became longer. However, since these are in vitro culture results, it is difficult to expect that the same properties would also be achieved in the intestine of animals.

EXAMPLE 4

Antibacterial Specrum Analysis

To investigate the antibacterial spectrum of the *Bacillus* sp. 2-4 strain of the present invention, the present inventors analyzed the antibacterial activity against various fish-pathogens through Halo test. Particularly, *Edwardsiella tarda, Streptococcus iniae, Vibrio anguillarum, Vibrio harveyi,* and *Streptococcus parauberis*, which are fish pathogenic microorganisms, were cultured in a media suitable for the growth of respective bacteria, then spread on the agar media containing the media, and subsequently a paper disc having the diameter of 0.8 cm was placed on the media. Thereafter, about 50 µl of a 5-fold concentrated culture supernatant obtained through centrifugation was dropped when the *Bacillus* sp. 2-4 strain of the present invention was cultured at 30° C. for 48 hours and thus has the bacterial concentration of $1.0 \times 10^8$ cfu/ml. Then, the resultant was cultured at 25-30° C. for 24-48 hours, and afterwards, the size of a clear zone thus formed was measured. As shown in FIG. 5, the result proved that the *Bacillus* sp. 2-4 strain of the present invention had the strong antibacterial activity against *E. tarda, S. iniae* and *V. anguillarum*, but weak antibacterial activity against *V. harveyi* and *S. parauberis*.

EXAMPLE 5

Analysis of Enzyme Secreting Ability

To confirm that the *Bacillus* sp. 2-4 strain of the present invention secretes a helpful enzyme, the present inventors investigated the degrading ability with respect to various substrates. First of all, to investigate the activity of protein and lipid degrading enzymes, the Bacillus sp. 2-4 strain of the present invention was spread on the media, in which skim milk and 1% of tricaprylin were spread, then was cultured at 30° C. for 24 hours, and it was observed whether a clear zone was formed around the strain spread portions. As shown in a and b of FIG. 6, it was observed that the clear zone was formed. Subsequently, to confirm that the strain of the present invention had amylase and carboxymethylcellulase (CMCase) activities, the present inventors placed a paper disc on the agar plates, in which water-soluble starch and carboxymethylcellulase were spread respectively, then dropped 50 μl of 5-fold concentrated culture supernatant of the strain of the present invention, which was used in Example 3, left the plates for 16 hours at room temperature, and observed whether the clear zone was formed or not. Resultantly, as shown in c and d of FIG. 6, the amylase and CMCase activities were observed. Since those enzymes help raised individuals efficiently digest feed by promoting the degradation of various biomass included in the feed, the nonpathogenic bacteria which secretes those enzymes has high applicability as the feed additive. Thus, it can be understood that the Bacillus sp. 2-4 strain of the present invention is also a very helpful strain in view of digestion and absorption of the feed.

EXAMPLE 6

Hatch Test of Fish Egg

In order for specific bacteria to be used as feed additives for fish, the bacteria should be non-pathogenic, and also do not influence the hatch of fish egg. Thus, the present inventors measured the hatching rate of Paralichythys olivaceus in the presence of the strain of present invention. Particularly, approximately 120 eggs of Paralichythys olivaceu, with 12 hours passed after fertilization put into a beaker which contains sterilized sea water; thereafter the strain of the present invention and E. tarda were inoculated at a concentration indicated in Table 2; and the hatching rate was measured after a day passed. As shown in table 3, the result demonstrated that the strain of the present invention did not have any influence on the hatch of egg of Paralichythys olivaceus. On the other hand, in the case of treating the eggs with high concentration of E. tarda, the number of dead individuals is increased. It can be understood that such a trend was suppressed when the strain of the present invention was added.

TABLE 2

The influence of Bacillus sp. 2-4 on the hatch of fish eggs

| Control group | E. tarda | Number of dead individuals | Number of survival individuals | Etc. |
|---|---|---|---|---|
| 1 × 10$^6$ (Bacillus sp. 2-4 treating group) | no E. tarda | 7 | 105 | |
| | 1 × 10$^5$ E. tarda | 9 | 111 | |
| | 1 × 10$^6$ E. tarda | 6 | 97 | |
| | 1 × 10$^7$ E. tarda | 5 | 110 | |
| E. tarda only treating group | no E. tarda | 7 | 100 | |
| | 1 × 10$^5$ E. tarda | 15 | 98 | |
| | 1 × 10$^6$ E. tarda | 8 | 102 | |
| | 1 × 10$^7$ E. tarda | 7 | 95 | |

TABLE 3

The effect of Bacillus sp. 2-4 on the vitality of rotifer

| | | Measuring the number of rotifer | | | | | | | | | | Average number of rotifer |
|---|---|---|---|---|---|---|---|---|---|---|---|---|
| | | 1 | 2 | 3 | 4 | 5 | 6 | 7 | 8 | 9 | 10 | |
| 1 | Control group | 7 | 7 | 6 | 6 | 6 | 6 | 5 | 6 | 5 | 7 | 6.1 |
| | 1 × 10$^6$ (Bacillus sp. 2-4 treating group) | 7 | 6 | 6 | 5 | 7 | 5 | 8 | 5 | 5 | 7 | 6.1 |
| 2 | Control group | 12 | 8 | 8 | 12 | 13 | 9 | 10 | 10 | 10 | 9 | 10.1 |
| | 1 × 10$^6$ (Bacillus sp. 2-4 treating group) | 12 | 9 | 9 | 12 | 12 | 8 | 7 | 10 | 8 | 9 | 9.6 |

EXAMPLE 7

Investigation of Influence on Vitality of Rotifer and Artemia

In order for bacteria to be used as feed additives for aquaculture of fish and crustaceans, the bacteria should not influence on the survival and vitality of rotifer and artemia which are main feeds for fish and crustaceans. Thus, the present inventors investigated the influence of the strain of the present invention on the vitality of rotifer and artemia. Particularly, the same numbers of rotifers were respectively put into a normal sterilized sea water (control group) and a sterilized sea water which was inoculated with 10$^6$ CFU/ml strain of the present invention, then left remaining for 24 hours at room temperature, and thereafter the number of rotifers alive was measured. As shown in table 2, the result proved that rotifers in the group inoculated with the strain of the present invention were not significantly different in vitality from those in the control group. Subsequently, the present inventors investigated the influence of the Bacillus sp. 2-4 strain of the present invention on the vitality of artemia, other planktons for feed. Specifically, the same number of artemia were respectively put into a normal sterilized sea water (control group) and a sterilized sea water which was inoculated with 10$^6$ CFU/ml of the strain of the present invention, then left remaining for 24 hours at room temperature, and thereafter the number of artemia alive was measured. As shown in table 4, the result proved that the strain of the present invention did not have any influence on the vitality of artemia.

TABLE 4

The influence of *Bacillus* sp. 2-4 on the vitality of artemia

| | | Measuring the number of *artemia* | | | | | | | | | | Average number of artemia |
|---|---|---|---|---|---|---|---|---|---|---|---|---|
| | | 1 | 2 | 3 | 4 | 5 | 6 | 7 | 8 | 9 | 10 | |
| 1 | Control group | 6 | 4 | 5 | 6 | 6 | 6 | 6 | 7 | 4 | 4 | 5.4 |
| | $1 \times 10^6$ (*Bacillus* sp. 2-4 treating group) | 4 | 6 | 5 | 4 | 5 | 4 | 6 | 5 | 6 | 6 | 5.1 |
| 2 | Control group | 5 | 4 | 6 | 6 | 5 | 4 | 8 | 6 | 4 | 5 | 5.3 |
| | $1 \times 10^6$ (*Bacillus* sp. 2-4 treating group) | 4 | 5 | 6 | 6 | 7 | 5 | 4 | 5 | 6 | 4 | 5.2 |

EXAMPLE 8

Probiotics Effect Analysis

To investigate that the strain of the preset invention served as probiotics when actually added in the feed and then supplied to fish, the present inventors actually mixed the strain of the present invention with the feed to supply the resultant mixture, then injected *E. tarda*, a representative fish pathogen, into intraperitoneal of *Paralichythys olivaceus*, and thereafter counted the number of dead individuals.

Figure 6:
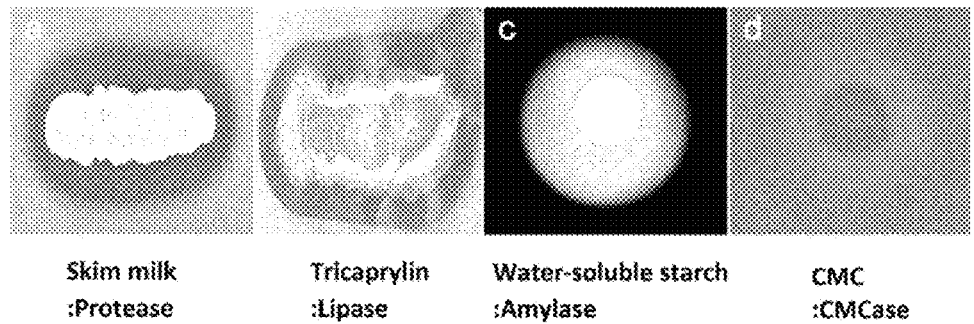
FIG. 6 is a photograph showing various enzyme productivities of the *Bacillus* sp. 2-4 strain of the present invention.

Specifically, feed was used by mixing a raw material shown in table 5, i.e., live bacterial preparation added feed with 0.5% by weight of culture powders of the strain of the present invention, and a control group was adjusted equally by adding cellulose. In the challenge test for verifying the live antibacterial preparation effect, 80 *Paralichthys olivaceus* for each group was fed for a month with control and live bacterial preparation added feed, respectively. $1 \times 10^6$ cells of *E. tarda* were intraperitoneally injected into the *Paralichthys olivaceus* and the accumulated number of dead individuals was documented while being raised at water temperature of 13-14° C. for 20 days. As a result, as shown in FIG. 6, the accumulated number of dead individuals was smaller in live bacterial preparation added group than those in the control group.

TABLE 5

Feed composition for verifying the probiotics effects

| Control gorup | | Live bacterial preparation | |
|---|---|---|---|
| Name of raw material | % | Name of raw material | % |
| Fishmeal | 65.6 | Fishmeal | 65.6 |
| Wheat meal | 20.4 | Wheat meal | 20.4 |
| Squid liver oil | 5.5 | Squid liver oil | 5.5 |
| Soybean meal | 3.0 | Soybean meal | 3.0 |
| Vitamine premix | 1.0 | Vitamine premix | 1.0 |
| Mineral premix | 1.0 | Mineral premix | 1.0 |
| CMC | 3.0 | CMC | 3.0 |
| cellulose | 0.5 | Live bacterial preparation (*Bacillus* sp. 2-4) | 0.5 |
| Total | 100 | Total | 100 |

Figure 7:
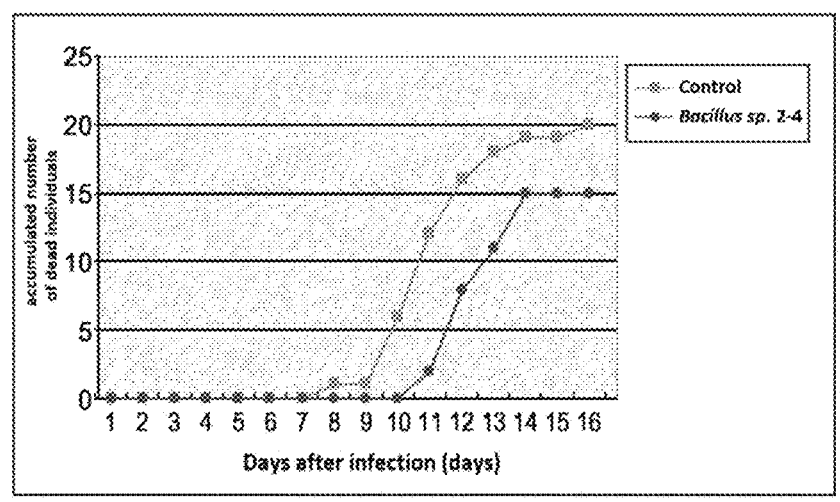
FIGS. 7 and 8 are graphs illustrating the in vivo antibacterial activity of the *Bacillus* sp 2-4 strain of the present invention.
Figure 8:
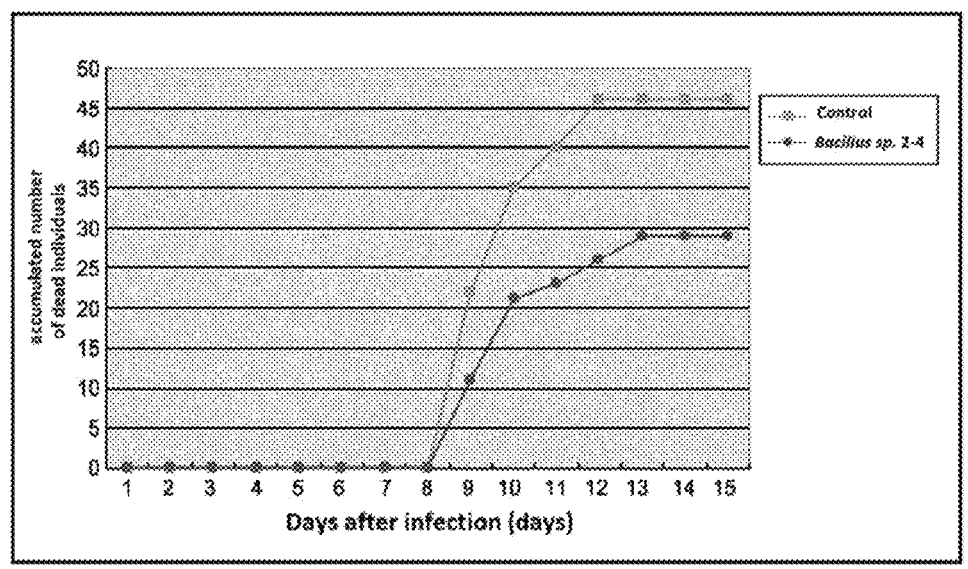

Also, to investigate seasonal differences, the present inventors fed *Paralichythys olivaceus* (110 for each group) with feed produced as indicated in table 5 for a month, then inoculate each group with $5 \times 10^5$ of *E. tarda*, and thereafter the accumulated number of dead individuals was documented while being raised at water temperature of 20-22° C. for two weeks. As a result, as shown in FIG. 7, the ratio of death of the group fed with the strain of the present invention was about 60% of the ratio of death of the control group. This proves that the strain of the present invention is effective for the prevention of massive death of fish even in summer when the fish infectious diseases frequently occur.

The isolated *Bacillus* sp. 2-4 according to an embodiment of the present invention can be usefully used as probiotics and the feed additive because the *Bacillus* sp. 2-4 exhibits the strong antibacterial activity against *Edwardisella tarda*, *Streptococcus iniae* and *Vibrio anguillarum*, which are fish pathogens, and also has the outstanding effect of secreting various enzymes which are helpful for body, while not exerting any influence on the hatch of fish and the vitality of rotifer and artemia which are feeds of fish.

Although an isolated *Bacillus* sp. probiotics strain has been described with reference to the specific examples, it is not limited thereto. Therefore, it will be readily understood by those skilled in the art that various modifications and changes can be made thereto without departing from the spirit and scope of the present invention defined by the appended claims.

SEQUENCE LISTING FREE TEXT

SEQ ID NO.1 is a base sequence of a 16S rDNA of the isolated *Bacillus* sp. 2-4 of the present

What is claimed is:

1. A method for inhibiting bacterial pathogens which cause massive death of farm-raised fish and/or crustaceans, the method comprising feeding farm-raised fish and/or crustaceans with an effective amount of an isolated *Bacillus* sp. 2-4 (KCCM11107P) strain.

* * * * *

```
                        SEQUENCE LISTING

<160> NUMBER OF SEQ ID NOS: 1

<210> SEQ ID NO 1
<211> LENGTH: 540
<212> TYPE: DNA
<213> ORGANISM: Bacillus sp. 2-4

<400> SEQUENCE: 1
agagtttgat cctggctcag gacgaacgct ggcggcgtgc ctaatacatg caagtcgagc      60
ggacagatgg gagcttgctc cctgatgtta gcggcggacg ggtgagtaac acgtgggtaa     120
cctgcctgta agactgggat aactccggga aaccggggct aataccggat ggttgtttga     180
accgcatggt tcagacataa aaggtggctt cggctaccac ttacagatgg acccgcggcg     240
cattagctag ttggtgaggt aacggctcac caaggcgacg atgcgtagcc gacctgagag     300
ggtgatcggc cacactggga ctgagacacg gcccagactc ctacgggagg cagcagtagg     360
gaatcttccg caatggacga aagtctgacg gagcaacgcc gcgtgagtga tgaaggtttt     420
cggatcgtaa agctctgttg ttagggaaga acaagtgccg ttcaaatagg gcggcacctt     480
gacggtacct aaccagaaag ccacggctaa ctacgtgcca gcagccgcgg taatacgtag     540
```